United States Patent
Nguyen et al.

(10) Patent No.: US 11,672,507 B2
(45) Date of Patent: Jun. 13, 2023

(54) SYSTEM AND METHOD FOR ULTRASOUND SHEAR WAVE ELASTOGRAPHY USING EXTERNAL MECHANICAL VIBRATIONS

(71) Applicants: KONINKLIJKE PHILIPS N.V., Eindhoven (NL); MASSACHUSETTS INSTITUTE OF TECHNOLOGY, Cambridge, MA (US)

(72) Inventors: Man Nguyen, Melrose, MA (US); Hua Xie, Cambridge, MA (US); Sheng-Wen Huang, Ossining, NY (US); Brian Anthony, Cambridge, MA (US); Heng Yang, Cambridge, MA (US)

(73) Assignees: KONINKLIJKE PHILIPS N.V., Eindhoven (NL); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 302 days.

(21) Appl. No.: 16/499,463

(22) PCT Filed: Mar. 30, 2018

(86) PCT No.: PCT/EP2018/058370
§ 371 (c)(1),
(2) Date: Sep. 30, 2019

(87) PCT Pub. No.: WO2018/178379
PCT Pub. Date: Oct. 4, 2018

(65) Prior Publication Data
US 2020/0060654 A1    Feb. 27, 2020

Related U.S. Application Data

(60) Provisional application No. 62/479,512, filed on Mar. 31, 2017.

(51) Int. Cl.
*A61B 8/08* (2006.01)
*A61B 8/14* (2006.01)
(Continued)

(52) U.S. Cl.
CPC ............ *A61B 8/485* (2013.01); *A61B 8/14* (2013.01); *A61B 8/4209* (2013.01);
(Continued)

(58) Field of Classification Search
CPC ......... A61B 8/485; A61B 8/14; A61B 8/4209; A61B 8/4254; A61B 8/5246;
(Continued)

(56) References Cited

U.S. PATENT DOCUMENTS

| | | | |
|---|---|---|---|
| 5,634,465 A * | 6/1997 | Schmiesing | G01S 15/58 73/861.25 |
| 6,343,250 B1 * | 1/2002 | Kuras | F16H 61/47 701/53 |

(Continued)

FOREIGN PATENT DOCUMENTS

| | | | |
|---|---|---|---|
| WO | 2010012092 A1 | 2/2010 | |
| WO | WO-2015141460 A1 * | 9/2015 | ............. A61B 8/485 |
| WO | 2016196631 A1 | 12/2016 | |

OTHER PUBLICATIONS

International Search Report and Written Opinion for International Application No. PCT/EP2018/058370, filed Mar. 30, 2018, 17 pages.

*Primary Examiner* — Yi-Shan Yang
*Assistant Examiner* — Nicholas A Robinson (57) ABSTRACT

Systems and methods for ultrasound shear wave elastography (SWE) are described. According to examples, an ultrasound SWE system includes an ultrasound probe (120), an actuation assembly (130) coupled to the probe and configured to apply an external force against a subject for gener-
(Continued)

ating a shear wave within a target region, a controller (140) coupled to the actuation assembly to control the actuation assembly to apply the force responsive to a trigger signal, and ultrasound scanner (110) configured to generate the trigger signal, and further configured to generate an elastography image based at least in part on echo signals received from the target region.

17 Claims, 9 Drawing Sheets (51) Int. Cl.
*A61B 8/00* (2006.01)
*G01S 7/52* (2006.01)
(52) U.S. Cl.
CPC .......... *A61B 8/4254* (2013.01); *A61B 8/5246* (2013.01); *A61B 8/5276* (2013.01); *A61B 8/54* (2013.01); *G01S 7/52042* (2013.01)

(58) Field of Classification Search
CPC ....... A61B 8/5276; A61B 8/54; A61B 5/0051; G01S 7/52042; G01S 7/52079; G01S 15/8915
See application file for complete search history.

(56) References Cited

U.S. PATENT DOCUMENTS

| 9,277,955 | B2* | 3/2016 | Herscher | A61B 18/1492 |
| 2004/0225215 | A1 | 11/2004 | Querleux et al. | |
| 2008/0200805 | A1 | 8/2008 | Hoyt et al. | |
| 2013/0131511 | A1* | 5/2013 | Peterson | G01S 7/52042 600/438 |
| 2014/0316267 | A1* | 10/2014 | Barry | A61B 8/4444 600/438 |
| 2017/0148437 | A1* | 5/2017 | Forsell | A61N 1/37211 |
| 2018/0256132 | A1* | 9/2018 | Halmann | A61B 8/488 |
| 2018/0296191 | A1* | 10/2018 | Mellema | A61B 8/5276 |
| 2019/0254629 | A1* | 8/2019 | Li | A61B 8/08 |

* cited by examiner

SYSTEM AND METHOD FOR ULTRASOUND SHEAR WAVE ELASTOGRAPHY USING EXTERNAL MECHANICAL VIBRATIONS

RELATED APPLICATIONS

This application is the U.S. National Phase application under 35 U.S.C. § 371 of International Application No. PCT/EP2018/058370, filed on Mar. 30, 2018, which claims priority to and benefit of U.S. Provisional Application Ser. No. 62/479,512, filed Mar. 31, 2017, which is incorporated by reference in its entirety.

TECHNICAL FIELD

The present disclosure pertains to ultrasound systems and methods for shear wave elastography, and more specifically to an ultrasound system and method operable to apply external mechanical vibrations to generate shear waves within a target region of a subject.

BACKGROUND

Ultrasound shear wave elastography (SWE), evaluating tissue elasticity by measuring shear wave speed, has become widely accepted as a non-invasive and quantitative diagnostic modality. Most SWE systems induce shear waves using acoustic radiation force (ARF). In a typical exemplary system, an initial, long ultrasound pulse, referred to as a push pulse, is applied to a tissue via ARF. The tissue may respond to the force of the push pulse by deforming. This deformation propagates through the tissue as one or more waves, referred to as shear waves. The propagation of the shear wave or waves through the tissue is monitored by additional ultrasound pulses, referred to as tracking pulses. Based on one or more factors (e.g., shear wave velocity, shear wave magnitude, and/or maximum propagation distance), a stiffness value of the tissue is calculated. An example of a stiffness value is the Young's modulus (E), typically measured in kPa. One method of calculating the elastic modulus is $E=3\rho(V_s)^2$, where $V_s$ is the shear wave propagation velocity in m/s and $\rho$ is tissue density in kg/m$^3$. Other methods of calculating a stiffness value of the tissue may be used. For example, the shear wave propagation velocity alone may be used as a measure of tissue stiffness.

Tissue stiffness measurements may be useful in disease diagnosis and/or monitoring. For example, in cirrhosis of the liver, diseased liver tissue has a higher stiffness than healthy liver tissue. Accordingly, shear wave elastography imaging may be used to diagnose or monitor liver disease. This may allow for improved diagnosis, monitoring and/or a reduction in the number of biopsies required. Similarly, shear wave imaging may be used to diagnose or monitor other diseases, such as breast lesion detection and thyroid nodule characterization As described, ARF-based shear wave elastography is generally commercially available only on high-end and premium ultrasound systems with transducers capable of generating high-voltage and long ARF push-pulses. Alternatively, the shear waves may be generated through external compression of the imaged tissue, which may provide the opportunity of carrying SWE for point of care and low resource settings. Externally induced shear waves are typically achieved by the sonographer externally compressing the tissue, typically with the ultrasound probe, and then rapidly acquiring images of the surrounding tissue. The images are then analyzed to detect and monitor the resulting shear wave or waves. Systems, which perform SWE based on externally applied force, may have shortcomings. Accordingly, users and manufacturers of ultrasound systems continue to seek improvements to the SWE imaging modality of such systems.

SUMMARY

The present application describes systems and methods for synchronized delivery of mechanical vibrations and shear wave elastography specific to the mechanical vibrations. Systems and methods of the invention accomplish shear wave elastography without the need for acoustic radiation forces to induce the shear waves. As a result, systems and methods of the invention enables shear wave elastography and its clinical benefits across a wide-range of ultrasound platforms (and not just those capable of inducing shear waves using acoustic radiation force).

In some embodiments, a system for ultrasound shear wave imaging according to the present disclosure may include a probe configured to transmit ultrasound signals toward a target region of a subject and receive echo signals responsive to the ultrasound signals, and actuation assembly coupled to the probe and configured to apply an external force against the subject for generating a shear wave within the target region, a controller coupled to the actuation assembly and configured to control the actuation assembly to apply the force responsive to a trigger signal and ultrasound scanner coupled to the probe and the controller, wherein the ultrasound scanner is configured to generate the trigger signal, and wherein the ultrasound scanner comprises at least one processor configured to generate an elastography image based at least in part on the echo signals.

According to some embodiments of the present disclosure, a method for shear wave imaging may include generating a plurality of line trigger signals by an ultrasound scanner operatively associated with a probe, receiving the plurality of line trigger signals by an actuation controller communicatively coupled to an actuator coupled to the probe, identifying a first trigger signal associated with a push pulse from the plurality of line trigger signals, transmitting a command to the actuator to apply a force against a medium being imaged, transmitting tracking ultrasound pulses and receiving echo signals by the probe to track propagation of a shear wave induced by the application of the force, and generating a shear wave image data, based at least in part, on the received echo signals.

DETAILED DESCRIPTION

The following description of certain embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

The present technology is also described below with reference to block diagrams and/or flowchart illustrations of methods, apparatus (systems) and/or computer program products according to the present embodiments. It is understood that blocks of the block diagrams and/or flowchart illustrations, and combinations of blocks in the block diagrams and/or flowchart illustrations, may be implemented by computer executable instructions. These computer executable instructions may be provided to a processor, controller or controlling unit of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

The present application describes systems and methods for synchronized delivery of mechanical vibration and shear wave elastography specific to the mechanical vibrations. Systems and methods of the invention accomplish shear wave elastography without the need for acoustic radiation forces to induce the shear waves. As a result, systems and methods of the invention enables shear wave elastography and its clinical benefits across a wide-range of ultrasound platforms (and not just those capable of inducing shear waves using acoustic radiation force). As noted, SWE is typically performed on high-end, expensive ultrasound systems capable of producing ARF pulse. External mechanical vibration (EMV) is an alternative for generating shear waves with potentially higher amplitudes, giving low-end systems an opportunity of carrying SWE for point of care and low resource settings. However, an ultrasound system, which can perform both conventional B-mode ultrasound imaging and EMV-enabled SWE imaging are currently not commercially available. The present disclosure describes examples of ultrasound imaging systems configured to perform shear wave imaging and specifically equipped with an actuation system configured to apply external mechanical vibrations for inducing shear waves in the target tissue. The auction system may be configured to operatively couple with any existing probe for example any of the ultrasound probes supplied by PHILIPS (e.g., the C5-1 probe or others).

In accordance with aspects of the present disclosure, the systems and methods described involve utilizing smart timing of the EMV during the period when the system expects the traditional acoustic radiation force pulse-pulses, and a shear wave speed reconstruction technique designed to account for the propagation directions of EMV-induced shear waves. Specifically, in some embodiments, the timing is accomplished by automatically detecting system trigger signals that may be associated with ARF based push-pulses and simultaneously and alternatively activating an external mechanical actuator. Furthermore, depending on the angle between the shear wave propagation direction(s) with respect to the imaging scan-lines, one or more directional filters and compensation for propagation angles may be applied during reconstruction steps for the proposed EMV-enabled SWE.

Figure 1:
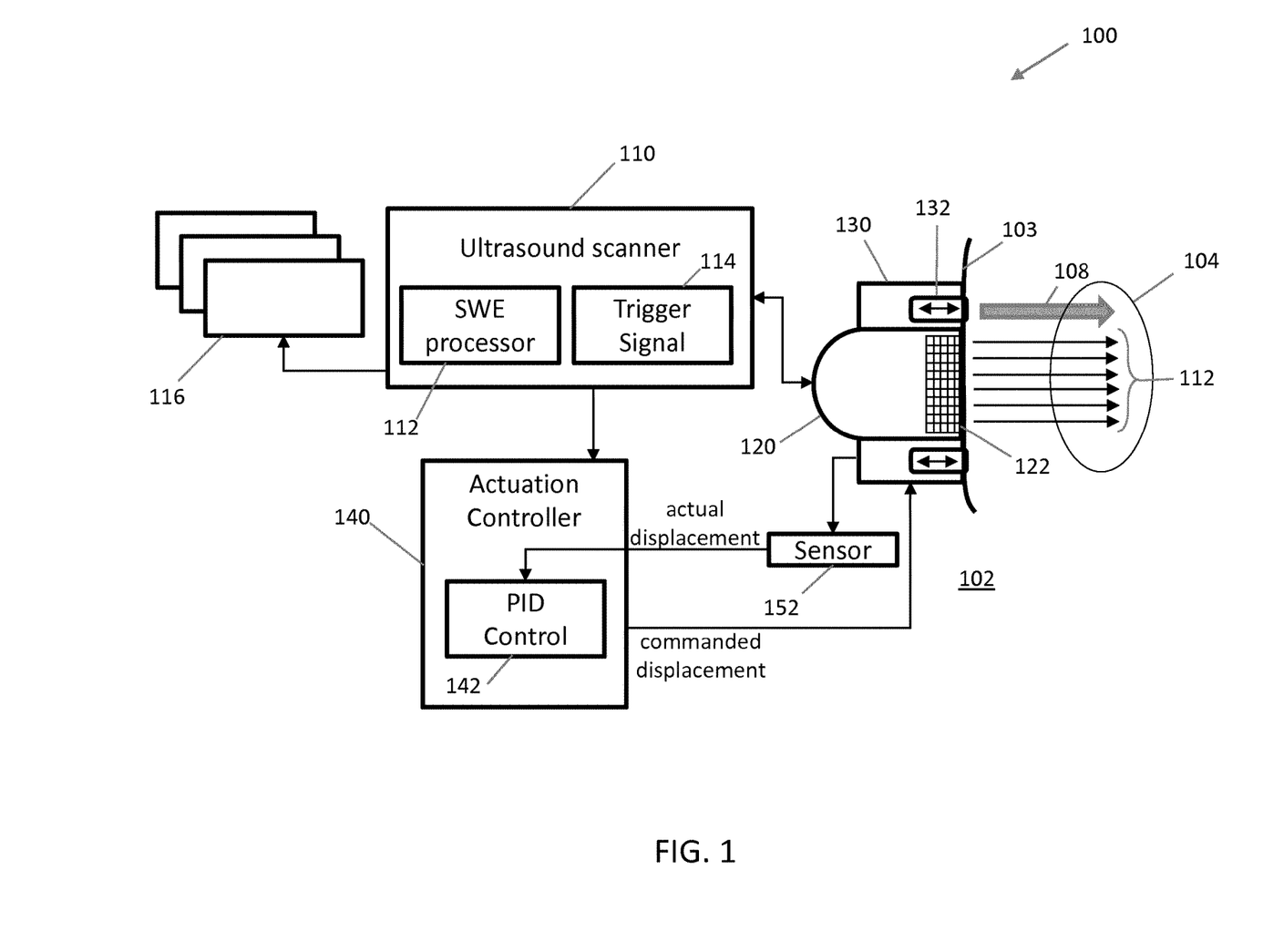
FIG. 1 shows a block diagram of an ultrasound imaging system according to examples of the present disclosure.

FIG. 1 shows, in block diagram form, an ultrasound shear wave elastography (SWE) system 100 configured to perform shear wave imaging in accordance with the principles of the present disclosure. The system 100 includes an ultrasound scanner 110 coupled to an ultrasound probe 120 and an external actuation assembly 130 coupled to the probe 120 and operatively associated with an actuation controller 140. The components and the arrangement thereof shown in FIG. 1 are merely illustrative, and other variations, including eliminating components, combining components, rearranging components, and substituting components are all contemplated.

The probe 120 includes a transducer array 122, which is configured to transmit ultrasound signals toward a target region 104 of a subject 102 (e.g., a patient) and receive echo signals responsive to the ultrasound signals. For example, when operating in shear wave imaging mode, the probe is configured to transmit tracking pulses 106 towards the target region 104 and receive echo signals responsive to the tracking pulses. The echo signals may be used to estimate the stiffness of the imaged medium (e.g., tissue stiffness of an imaged region of the subject, for example for monitoring patient treatment or making a diagnosis).

The probe 120 is communicatively coupled (e.g., via a wired connection provided by a probe cable or via a wireless connection) to an ultrasound scanner 110. The ultrasound scanner 110 is configured to perform both conventional B-mode imaging and shear wave imaging. For the latter, the ultrasound scanner 110 may include a SWE processor 112 operable to receive the ultrasound echoes (e.g., responsive to the ultrasound tracking pulses) and estimate the velocity of the shear wave propagating thought the tissue. The scanner 110 may also include a trigger signal generator 114 configured to provide a trigger signal for controlling the actuation assembly 130.

The probe 120 is coupled to an actuation assembly 130. The actuation assembly 130 includes at least one end-effector 132 configured to apply a force against the subject. For example, the actuation assembly may be configured to apply an oscillating force (e.g., responsive to oscillatory motion (i.e., vibration) of the end-effector 132) against the skin 103 of the patient for generating a shear wave within the target region (e.g., the target tissue being imaged). While force is being applied with the end-effector 132, the probe 120 is acoustically coupled and held stationary against the subject. In some embodiments, the actuation assembly may include multiple end-effectors 132, which may be configured to press against the subject in synchrony or at different times in order to induce a shear wave in the imaged region.

The system 100 further includes an actuation controller 140 operatively associated with the ultrasound scanner 110 and the actuation assembly 130. The controller 140 is configured to generate control signals based on trigger signals provided by the ultrasound scanner 110 for controlling the movement of the one or more end-effectors 132 of the actuation assembly 130. As such, the controller 140 is operatively coupled to the actuation assembly 130 to control the end-effector responsive to a trigger signal provided by the scanner 110. The actuation controller 140 may include a feedback logic circuit (e.g., a PID controller 142) configured to reduce the error between commanded and actual movement of the end effector(s) 132. To that end, the actuation controller 140 and/or the actuation assembly 130 may include or be operatively associated with a sensor 152 configured to measure the actual displacement and thus couple a signal representative of the actual displacement to the actuation controller 140. As described in more detail below, the ultrasound scanner is coupled to the probe and the controller and configured to generate the trigger signal. The ultrasound scanner is further configured to generate one or more elastography images 116 based at least in part on the echo signals received from the probe.

Figure 2:
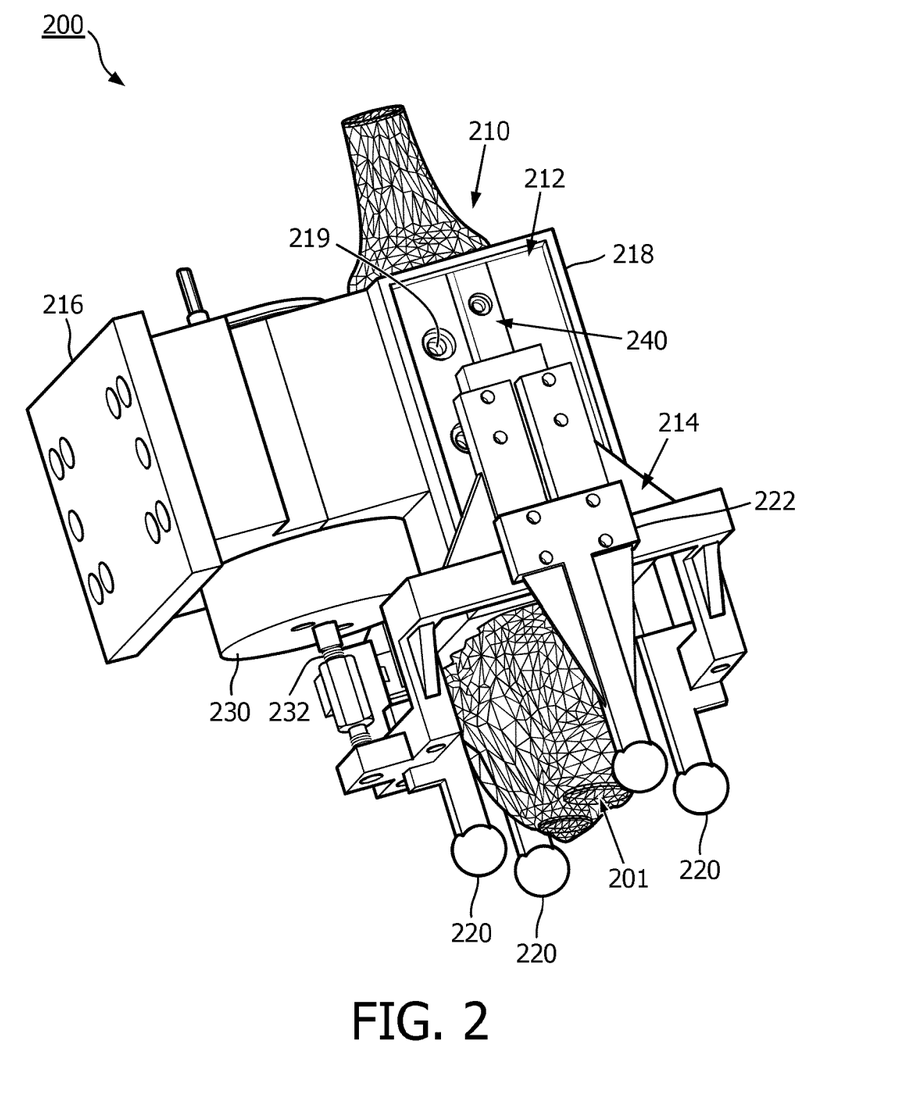
FIG. 2 illustrates an actuation assembly according to some examples of the present disclosure.

FIG. 2 shows an actuation assembly 200 in accordance with some examples of the present disclosure. The actuation assembly is coupled to an ultrasound probe 201. The actuation assembly 200 in this example includes a frame 210 including a stationary portion 212 and a movable portion 214, one or more end-effectors 220, a motor 230, and an interface 240 between the stationary and movable portions 212, 214 of the frame 210. The components and the arrangement thereof shown in FIG. 2 are merely illustrative, and other variations, including eliminating components, combining components, rearranging components, and substituting components are all contemplated.

The end-effector(s) 220 may be mechanically mounted to the probe 201 via the frame 210. The frame 210, and more specifically the stationary portion 212, may be configured to be attached to the probe, e.g., using friction. Ultrasound probes are generally designed to be handled by a user and thus typically have irregular, contoured surface, designed with ergonomic considerations in mind. The frame 210 may therefore be equipped with a holder 218, which has a contact surface having a complementary shape to the outer surface of the probe 201. The holder 218 may be part of the stationary portion 212 and may be integral therewith or separable from the stationary portion 212 of the frame 210. The holder 218 may be configured to mount to a specific probe (i.e., having a matching surface to that of a given probe) or it may be reconfigurable such as by having one or more surfaces which are adjustable (e.g., resiliently or reversibly moldable) to any given probe surface. The holder 218 may be of a two-part or clamshell design and may be held against the probe 201 via one or more fasteners 219, which can be used to tension the two parts of the holder 218 towards one another such as to maintain the probe 201 in frictional engagement with the contact surface of the holder 218. The holder 218 may thus function as a clamp to secure the frame 210 to the probe 201.

As shown in the illustrated example, the actuation assembly 200 includes at least one end-effector 220, which is supported on the movable portion 214 of the frame 210. The actuation assembly 200 may be configured to accommodate multiple end-effectors 220, each of which may be individually removably coupled to the movable proton 214, e.g., via a coupling flange 222. The movable portion 214 is configured to move in relation to the stationary portion 212, which remains generally stationary during imaging. In some examples, the stationary portion 212 may be coupled to a gantry e.g., via a base plate 216. The gantry may be used to position the probe 201 and actuation assembly 200 (either manually or responsive to electronic control) against the subject (e.g., against the patient's skin). The movable portion 214 is movably coupled to the stationary portion 212 via an interface 240. The interface 240 may be implemented using e.g., a linear bearing or any other type of a low friction slidable interface (e.g., an air bearing).

As further shown in the illustrated example, the actuation assembly 200 includes a motor 230, which may be supported on the stationary portion 212 of the frame 210. The driving member 232 (e.g., a rotary or linear shaft) of the motor 230 is coupled to the movable portion 214 of the frame to power the reciprocating movement of the end-effector(s) 220. In some embodiments, the motor 230 may be implemented using a voice coil actuator or any other type of motor providing high precision, low friction actuation of the movable portion of the assembly. Depending on the specific application and requirements (e.g., desired amplitude of vibrations, power consumption, etc.) a motor having any suitable size, power draw, weight, friction, pumping power, etc. may be used in other examples.

Figure 3:
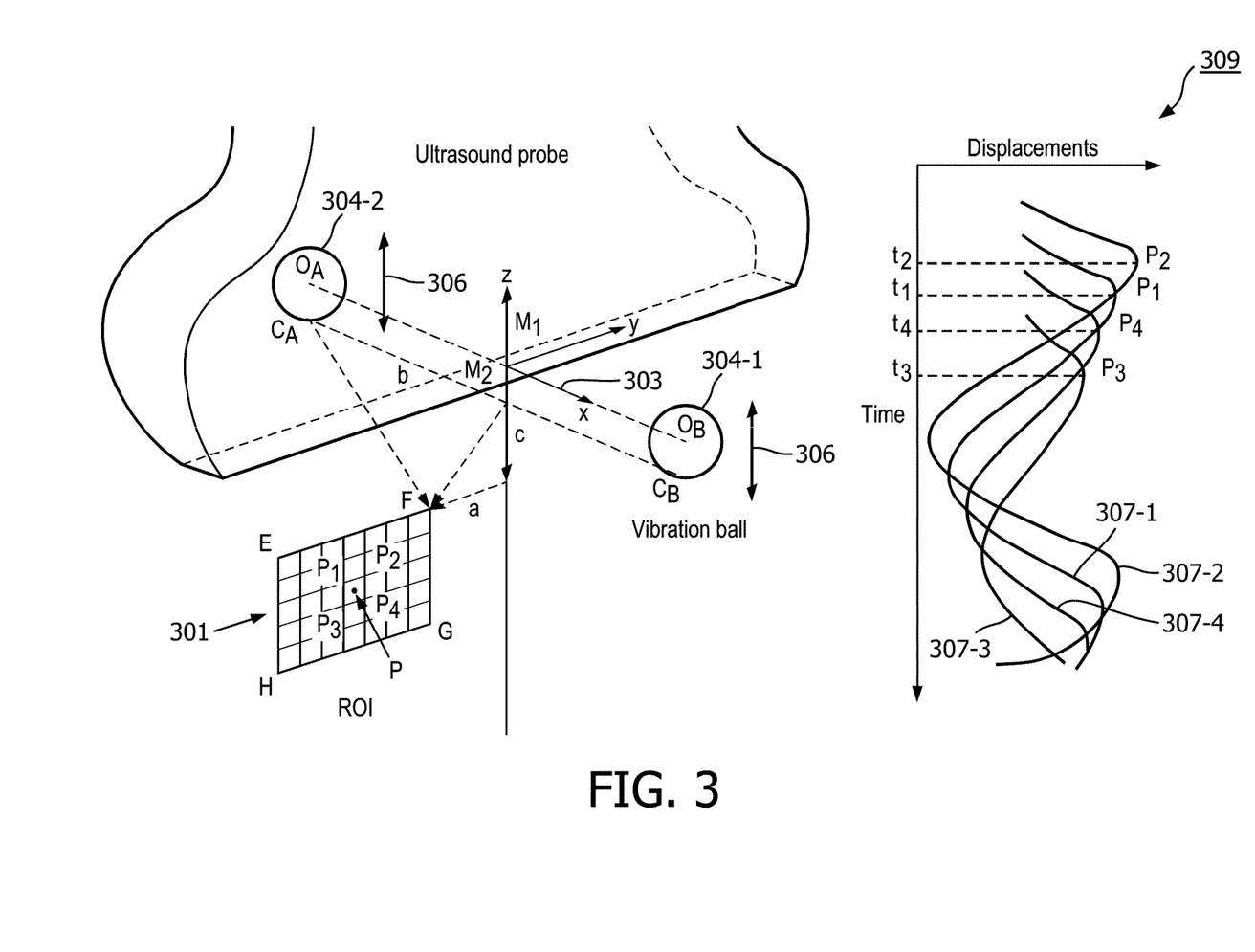
FIG. 3 illustrates concepts for shear wave speed estimation in accordance with principles of the present disclosure.

As described, the one or more end-effectors 220 may be individually removable from the frame 210 such that the actuation assembly may be configured for use with a single end-effector, or with a plurality of end-effectors, for example with four end-effectors as shown in FIG. 2, with two end-effectors in a cross-plane configuration as shown in FIG. 3, or with two end-effectors in an in-plane configuration, in which the end-effectors are arranged at the opposite longitudinal ends of the probe. Other configurations, such as using three end-effectors (e.g., one on each of three sides of the probe), or any other number of end-effectors (e.g., using multiple end-effectors on a given side of the probe) may also be used. The end-effectors may have a contact surface configured to applying sufficient mechanical force while minimizing patient discomfort. For example, a ball-shaped end-effector may be used, which may enable the application of a point force without significant discomfort to the patient. The end-effectors and any of the frame components may be manufactured from a rigid plastic material, e.g., to withstand deformation by the external resistance of the human tissue. For example, the end-effectors and any of the frame components may be manufactured from materials including acrylonitrile butadiene styrene (ABS), polylactic acid (PLA), polyamide (PA), polycarbonate (PC) and any other suitable thermoplastic or thermosetting polymer, for example using additive manufacturing techniques (e.g., 3D printing) or any conventional molding and machining techniques. Other suitable materials may be used.

FIG. 3 shows an illustration of shear wave speed estimation in an imaging plane 301 where shear wave propagation is induced by two vibration balls 304-1, 304-2 placed in a cross-plane configuration with respect to the transducer (i.e., with the vibration balls 304-1, 304-2 arranged along the short axis 303 of the probe, also referred to as elevation direction). Shear wave speed estimation, e.g., as described with reference to FIG. 3 and/or in combination with any known or later developed technique for shear wave speed estimation may be implemented, via hardware circuitry or software programming, in the SWE processor 112 of ultrasound scanner 110. As shown in FIG. 3, the centers of the two vibrating balls are indicated as $O_A$ and $O_B$, and the contact points between the two balls and the imaged medium are indicated as $C_A$ and $C_B$. The direction of movement or actuation of the vibration balls is indicated by arrows 306. The region of interest (ROI) is shown as a grid of pixels designated by EFGH at the corners of the example grid. It will be understood however that the size of the grid in the illustration, in this case 7×5, is for illustration purposes only and in practice the size of the ROI may be different, typically greater, although in some embodiments it may be smaller than the illustrated example. For each pixel ($P_i$) in the ROI, shear wave induced motion may be estimated in slow time. As an example only, the local displacement profiles of points $P_1$, $P_2$, $P_3$, and $P_4$ are shown in the plot 309 on the right side of FIG. 3. Specifically, referring to plot 309, the curve 307-1 shows the displacement of point $P_1$ as a function of time, the curve 307-2 shows the displacement of point $P_2$ as a function of time, the curve 307-3 shows the displacement of point P3 as a function of time, and the curve 307-4 shows the displacement of point $P_4$ as a function of time. To estimate the local elasticity at a given point P, shear wave delay and speed may be estimated in the lateral (x) and axial (c) directions using points around the P, e.g., points including $P_1$, $P_2$, $P_3$, and $P_4$, or a different group or number of points. Shear wave speed estimation based on the tracked displacements of points in the imaged region is generally known in the art, and any time-of-flight based method, for example time-to-peak (TTP), can be applied to calculate shear wave propagation delay. Assuming purely elastic tissue, elasticity (Young Modulus) is reconstructed from speed by using $E=3\rho(V_S)^2$ where $\rho$ denotes tissue density, and $V_S$ denotes the speed of the shear wave.

Figure 4:
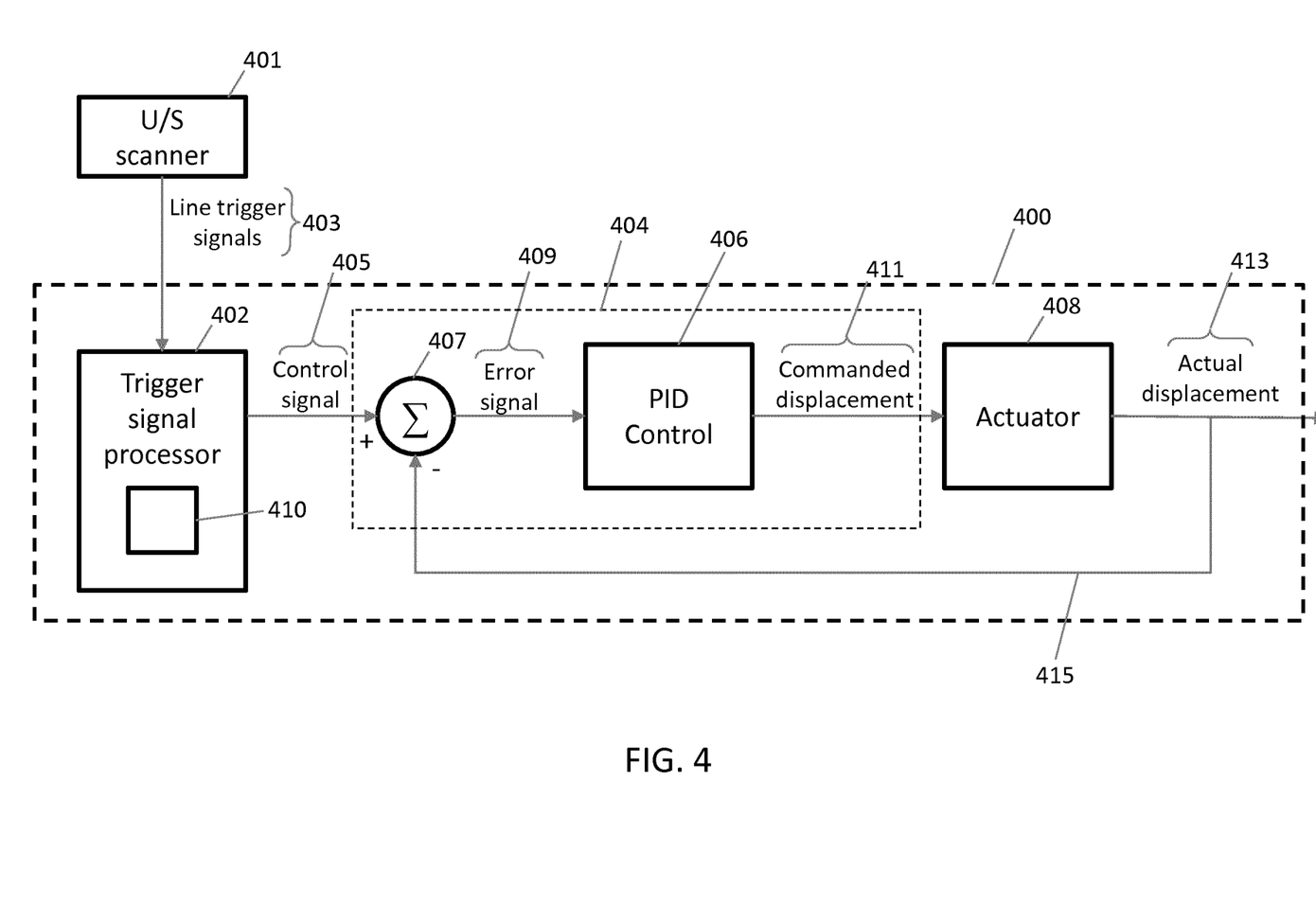
FIG. 4 shows a block diagram of an actuation controller according to some examples of the present disclosure.

FIG. 4 shows components of an actuation controller 400 according to some examples herein. The actuation controller 400 may be used to implement actuation controller 140 in FIG. 1. The actuation controller 400 may be configured, using one or more application-specific integrated circuits (ASICs) and/or programmable modules, to retrieve a trigger signal from the ultrasound scanner 401 and to couple the trigger signal to a control circuit, which applies a vibration trigger to the actuator 408. The actuation controller 400 may include a PID controller 406 configured to reduce or minimize the error (e.g., error signal 409) between the commanded displacement 411 and actual displacement 413 of the end-effector(s) of actuator 408. The components and the arrangement thereof shown in FIG. 4 are merely illustrative, and other variations, including eliminating components, combining components, rearranging components, and substituting components are all contemplated.

As shown in FIG. 4, the ultrasound scanner 401 generates line trigger signals 403, which are used by the ultrasound scanner 401 for generating image data as described further below. The line trigger signals 403 are also coupled to an input of the actuation controller 400. The actuation controller 400 includes a trigger signal processor 402, which is configured to extract a push-pulse trigger signal from the plurality of line trigger signals, as will be discussed further below with reference to FIGS. 5 and 6. The signal processor 402 generates a control signal 405 responsive to the push-pulse trigger signal and couples the control signal 405 to a control circuit 404 that generates commands to cause the actuator to displace the end-effector(s) of actuator 408. The control circuit 404 includes a proportional-integral-derivative (PID) controller 406, which implements a feedback loop 415 designed to reduce the error between the commanded displacement 411 and actual displacement 413. The actual displacement 413 is measured (e.g., via a sensor operatively coupled to the motor or integral therewith) at the output end of the actuator 408 and is coupled to a summation block 407 that computes the error signal between the control signal, which corresponds to the commanded or desired displacement, and the measured signal, which correspond to the actual displacement e.g., as may be affected by any imperfections in the system and/or external disturbances. The error signal 409 is coupled to the PID controller 406 for computing corrections to be applied to the control signal by the PID controller 406.

Figure 5:
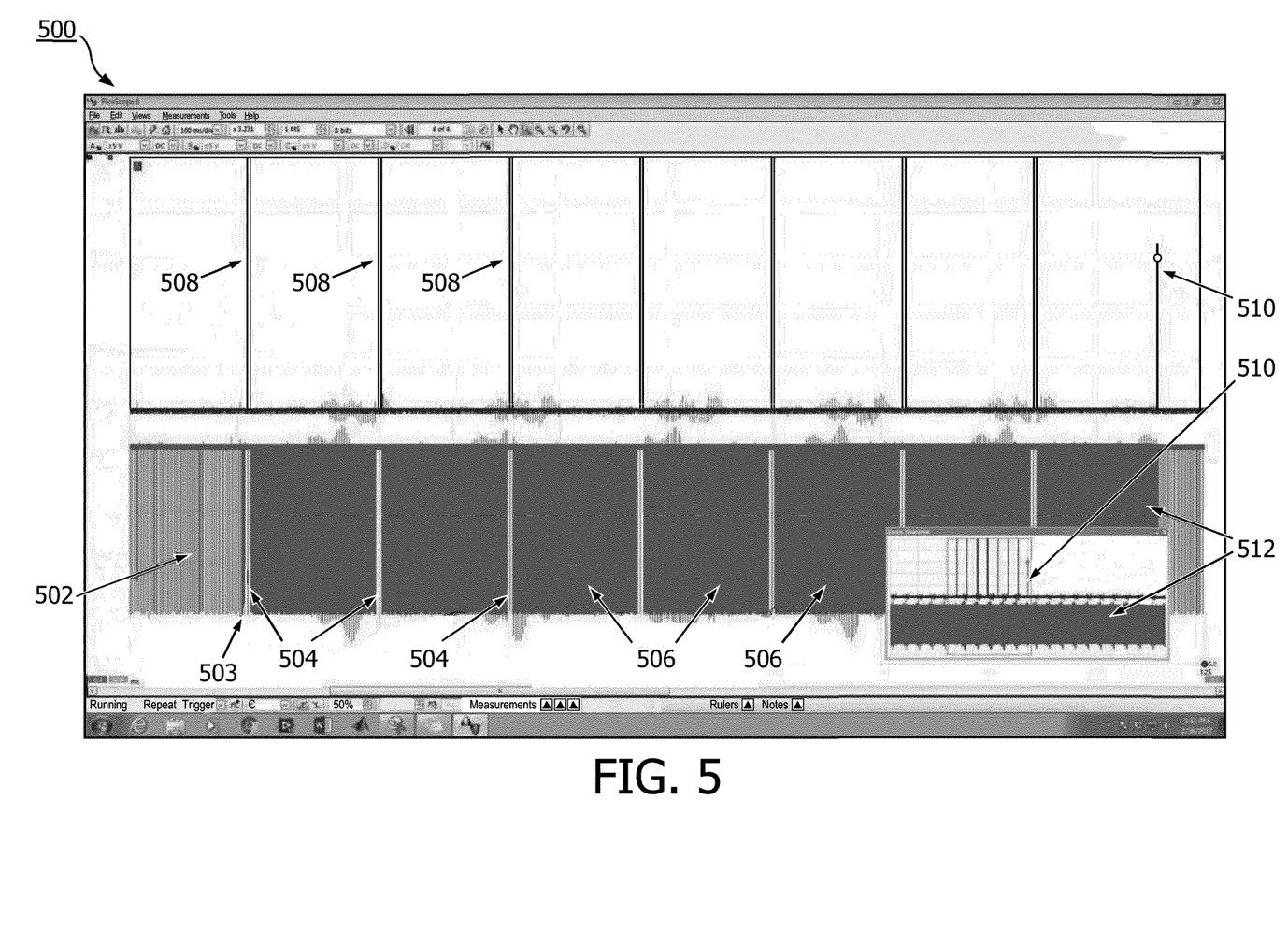
FIG. 5 illustrates control signal extraction from line trigger signals produced by an ultrasound scanner in accordance with principles of the present disclosure.

FIG. 5 shows a diagram 500 of line trigger signals generated by an ultrasound scanner, as may be utilized by a system according to the present disclosure for synchronizing external mechanical vibrations with internal ultrasound pulse triggers. As described, an ultrasound scanner according to the present disclosure (e.g., ultrasound scanner 110 (FIG. 1) or 401 (FIG. 4)) may be configured to generate a sequence of line trigger signals when operating in a shear wave imaging mode. The line trigger signals may be used by the ultrasound scanner to control an ultrasound probe to transmit and receive ultrasonic signals toward and from the imaged medium for generating shear wave images.

In some examples, the ultrasound scanner may generate B-mode line trigger signals that are utilized by the ultrasound scanner for controlling an ultrasound probe to transmit and receive ultrasound pulses and echoes, respectively, for acquiring B-mode image data. The ultrasound scanner may generate B-mode line trigger signals during conventional B-mode imaging as well as during shear wave imaging for acquiring anatomy information (e.g., for display concurrently with the tissue elasticity information, as shown for example in FIG. 8). Additionally, in the shear wave imaging mode, the ultrasound scanner is operable to generate a series of line trigger signals for acquiring shear wave imaging data. In conventional shear wave imaging systems which employ acoustic radiation force for shear wave generation, shear wave imaging is typically performed at frame rates of about 1 Hz (e.g., due to thermal stresses applied by the ARF), which is an order of magnitude slower than regular B-mode imaging. Thus, the user of ARF may impose a frame rate limitation on the imaging, which problem may be overcome by the examples herein. Since the examples herein rely on externally induced shear waves and thus are not associated with thermal stress on the imaged tissue, higher frame rates, up to as high as may be used in conventional B-mode imaging, may be applied also during shear wave imaging. Moreover, externally applied stimulation may reduce the cost of the system as the need for high-end ultrasound hardware capable of producing high voltage ARF push beams is obviated by the external actuator.

Referring back to FIG. 5, the illustration shows a sequence of line trigger signals that may be produced by an ultrasound scanner according to some examples herein. The plurality of line trigger signals 512 may include B-mode line trigger signals 502, push pulse line trigger signals 504, and tracking pulse line trigger signals 506. For each image frame, as indicated by frame trigger signal 510, a sequence of B-mode pulse-echo (i.e., transmit/receive) trigger signals are generated and coupled to a transmit controller and/or transmit/receive beamformer(s) of the ultrasound scanner to control the probe to transmit and receive ultrasound signals for generating B-mode image data. The B-mode image data is used to produce a B-mode (i.e., grayscale) image of the anatomy, typically displayed in the background and overlaid with the shear wave imaging data. For the latter, when imaging in SWE mode, the ultrasound scanner follows the series of B-mode trigger signals with a sequence of shear wave imaging trigger signals. The shear wave imaging trigger signals include one or more push pulse trigger signals followed by a plurality of tracking pulse trigger signals. In a conventional ARF-based system, both the push pulse and the tracking pulse trigger signals are coupled to the transmit controller and/or beamformer(s) to configure the probe to first transmit a push pulse followed by configuring the probe to transmit tracking pulses and receive echo signals responsive to the tracking pulses.

In accordance with the examples herein, the ultrasound scanner may be programmed to generate a sequence of trigger signals for performing SWE, e.g., as shown in FIG. 5, whether or not the system is capable of producing a push pulse. If the scanner is capable of producing push pulses, when performing SWE imaging with external vibrations, the push pulse functionality may be disabled (e.g., at the transmit controller and/or beamformer). The line trigger signals are additionally coupled to the actuation controller to extract the appropriate trigger signals and thus synchronize timing of the external vibrations with the timing expected by the system (e.g., as if operating in conventional ARF-based mode).

As will be appreciated from FIG. 5, the temporal spacing of the different types of trigger signals may vary based on the type of trigger signal being generated by the system. For example, the time gaps 503 around the push pulse trigger signals (e.g., before and/or after the generation of a push pulse) may be longer, typically significantly longer than the time gaps between consecutive B-mode or tracking pulse trigger signals. Accordingly, this difference in the temporal spacing may be used to identify the push pulse triggers from the series of triggers generated by the ultrasound scanner during SWE imaging.

Figure 6:
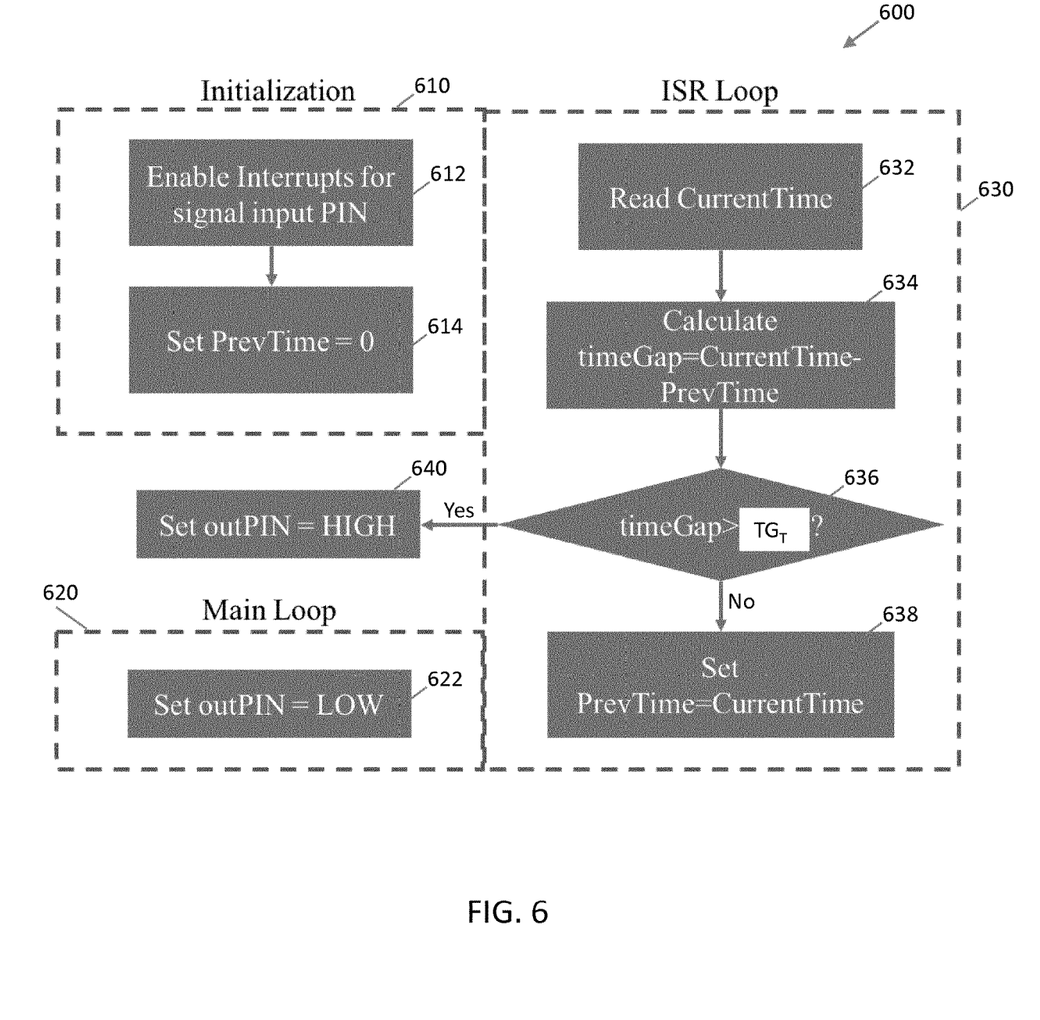
FIG. 6 is a flowchart of a method according to principles of the present disclosure.

FIG. 6 shows a logic diagram of a signal processor configured to extract a push pulse trigger for generation vibration control signal from line trigger signals output by an ultrasound scanner. The signal processor 600 may be used to implement the trigger signal processor 402 of FIG. 4, for example. The blocks and the arrangement thereof shown in FIG. 6 are merely illustrative, and other variations, including eliminating components, combining components, rearranging components, and substituting components are all contemplated.

In the example in FIG. 6, the signal processor 600 includes an initialization block 610. The initialization block 610 includes enabling an interrupt service routine (ISR) for the input signal received via an input of signal processor 600 (e.g., as shown in block 612) and setting the previous time to zero (e.g., by setting PrevTime memory location to 0), as shown in block 614. The main logic loop 620 of signal processor 600 includes the steps of setting the output to low as shown in block 622. Each time the input is driven high by a line trigger signal, the signal processor enters an ISR loop 630, in which the processor 600 calculates a time gap between the current line trigger signal and the previous line trigger signal. The processor 600 may be configured to identify a push pulse trigger if the time gap (e.g., 503 in FIG. 5) exceed a given threshold $TG_T$, for example 700 μs. The threshold $TG_T$ may be different in other examples, for example anywhere between about 550 μs up to about 950 μs or greater, or other as further described below.

As shown in the example in FIG. 6, the ISR loop 630 performs the following steps starting with reading the current time associated with the incoming or current line trigger signal, as shown in block 632. The current time may be stored in a first memory location (e.g., of memory 410 of the processor 402 in FIG. 4), also referred to as CurrentTime memory location. The processor 600 calculates, as shown in block 634, the time gap by computing the difference between the current time and the previous time, which is the time associated with the previous line trigger signal. The value of the time gap (timeGap) is stored in a second memory location. The processor 600 determines if the value (timeGap) exceeds the threshold value ($TG_T$), as shown in decision block 636. If the value (timeGap) exceeds the threshold value ($TG_T$), the processor sets the output signal to high, as shown in block 640. If the value (timeGap) does not exceed the threshold value ($TG_T$), the processor 600 sets the value of the PrevTime memory location to the value stored in the CurrentTime memory location, as shown in block 638. By driving the output of processor 600 high, a control signal (e.g., signal 405) is generated any time the processor 600 identifies a push pulse from among the plurality of line trigger signals. The processor 600 may be configured to perform signal processing in accordance with the logic described herein for every incoming line trigger signal when the ultrasound scanner is operating in shear wave imaging mode.

As the number of time gaps and/or the spacing between the line trigger signals, and thus the time gap separating the push pulse line trigger signal from surrounding line trigger signals, for a given image frame may vary between different imaging applications, the internal logic of processor 600 may be differently configured for other applications, e.g., by setting a different threshold ($TG_T$). In some embodiments, the processor 600 may be configured to apply a different threshold depending on the application (e.g., when imaging different types of tissue and/or at different depths within the medium). For example, the processor 600 may be operatively coupled to a fourth memory location storing a plurality of threshold ($TG_T$) values, each associated with a different imaging application. The ultrasound scanner may be further configured to couple an application-select ($SEL_A$) signal to the processor 600, e.g., responsive to activation of any one of a plurality of imaging applications, typically responsive to user input. The processor may retrieve, from the fourth memory location, the threshold ($TG_T$) value associated with the received $SEL_A$ signal and apply the selected threshold ($TG_T$) value in the ISR loop 630 until termination of the imaging session or until a different $SEL_A$ signal is received.

Figure 7:
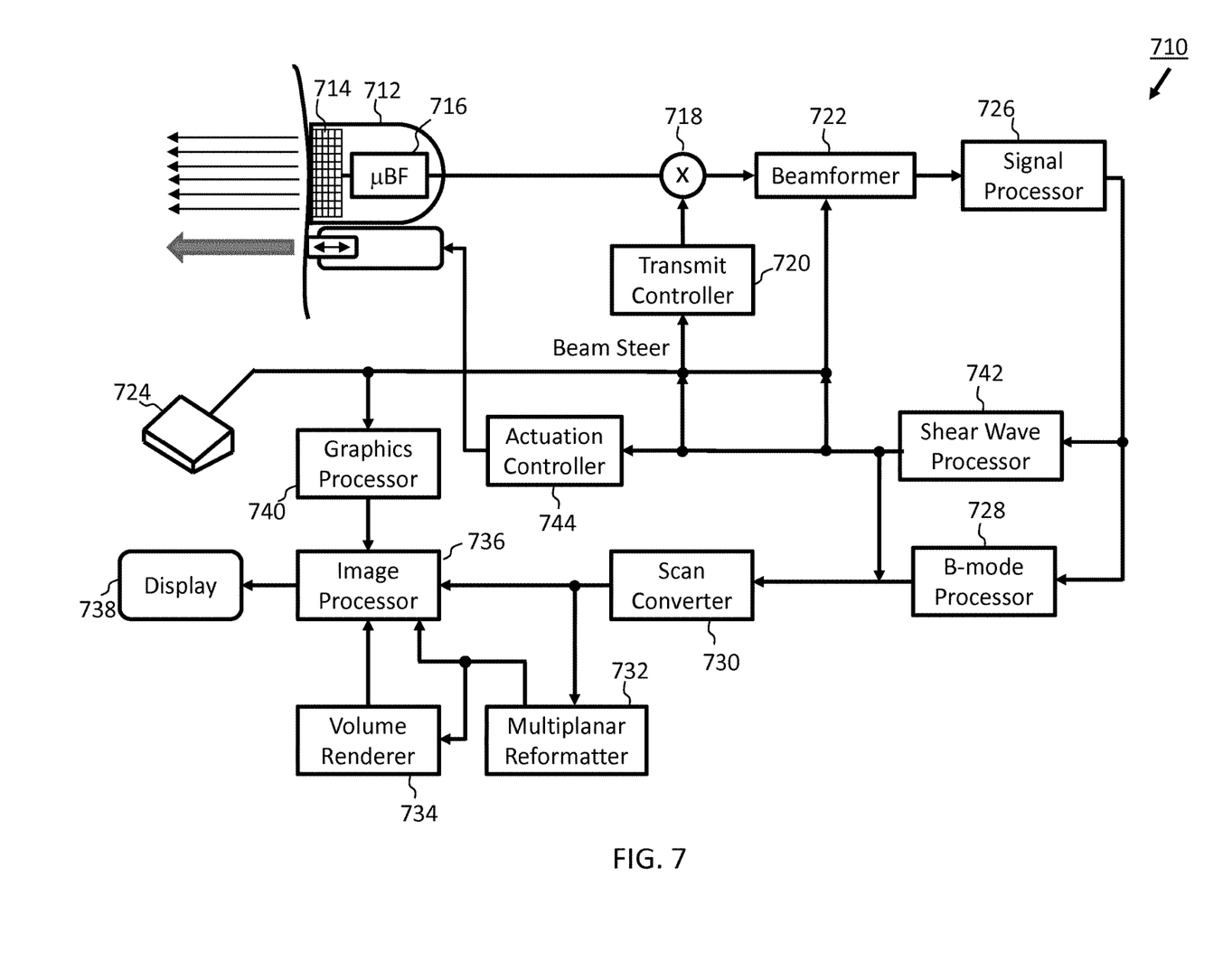
FIG. 7 is a block diagram of an ultrasound imaging system according to further examples of the present disclosure.

FIG. 7 shows a bock diagram of an ultrasound imaging system 710 in accordance with embodiments of the present disclosure. The ultrasound imaging system 710 may include an ultrasound imaging device (e.g., also referred to herein as ultrasound scanner) configured to receive a shear wave signal for performing shear wave imaging. The ultrasound imaging device may include processing components (e.g., one or more beamformers, signal processor, etc.) communicatively coupled to an ultrasound probe operable to transmit ultrasound and receive echoes from a subject. The components and the arrangement thereof shown in FIG. 7 are merely illustrative, and other variations, including eliminating components, combining components, rearranging components, and substituting components are all contemplated.

As shown in FIG. 7, the ultrasonic imaging system 710 may include an ultrasound probe 712 includes a transducer array 714 for transmitting ultrasound signals toward a target region of a subject and receiving echo signals responsive to the ultrasound signals. A variety of transducer arrays are known in the art, e.g., linear arrays, convex arrays or phased arrays. The transducer array 714, for example, can include a two dimensional array (as shown) of transducer elements capable of scanning in both elevation and azimuth dimensions for 2D and/or 3D imaging. The transducer array 714 may be coupled to a microbeamformer 716 in the probe 712, which controls transmission and reception of signals by groups of transducer elements in the array. In this example, the microbeamformer is coupled by the probe cable to a transmit/receive (T/R) switch 718, which switches between transmission and reception and protects the main beamformer 722 from high energy transmit signals. In some embodiments, the probe may be coupled to the signal and image processing components, typically located in an ultrasound system base, wirelessly. In some embodiments, the T/R switch 718 and other elements in the system can be included in the transducer probe rather than in the separate ultrasound system base. The transmission of ultrasonic beams from the transducer array 714 under control of the microbeamformer 716 is directed by the transmit controller 720 coupled to the T/R switch 718 and the beamformer 722, which receives input from the user's operation of the user interface or control panel 724. One of the functions controlled by the transmit controller 720 is the direction in which beams are steered. Beams may be steered straight ahead from (orthogonal to) the transducer array, or at different angles for a wider field of view. The partially beamformed signals produced by the microbeamformer 716 are coupled to a main beamformer 722 where partially beamformed signals from individual patches of transducer elements are combined into a fully beamformed signal.

The beamformed signals are coupled to a signal processor 726. The signal processor 726 can process the received echo signals in various ways, such as bandpass filtering, decimation, I and Q component separation, and harmonic signal separation. The signal processor 726 may also perform additional signal enhancement such as speckle reduction, signal compounding, and noise elimination. The processed signals are coupled to a B-mode processor 728, which can employ amplitude detection for the imaging of structures in the body. The signals produced by the B-mode processor are coupled to a scan converter 730 and a multiplanar reformatter 732. The scan converter 730 arranges the echo signals in the spatial relationship from which they were received in a desired image format. For instance, the scan converter 730 may arrange the echo signal into a two dimensional (2D) sector-shaped format, or a pyramidal three dimensional (3D) image. The multiplanar reformatter 732 can convert echoes, which are received from points in a common plane in a volumetric region of the body into an ultrasonic image of that plane, as described in U.S. Pat. No. 6,443,896 (Detmer). A volume renderer 734 converts the echo signals of a 3D data set into a projected 3D image as viewed from a given reference point, e.g., as described in U.S. Pat. No. 6,530,885 (Entrekin et al.) The 2D or 3D images are coupled from the scan converter 230, multiplanar reformatter 732, and volume renderer 734 to an image processor 736 for further enhancement, buffering and temporary storage for display on an image display 738. The graphics processor 736 can generate graphic overlays for display with the ultrasound images. These graphic overlays can contain, e.g., standard identifying information such as patient name, date and time of the image, imaging parameters, and the like. For these purposes the graphics processor receives input from the user interface 724, such as a typed patient name. The user interface can also be coupled to the multiplanar reformatter 732 for selection and control of a display of multiple multiplanar reformatted (MPR) images.

The system further includes an actuation system 750 operatively associated with the ultrasound probe 712. The actuation system 750 is configured to apply an external force to the subject 701 (e.g., externally applied push pulse 702) to induce a shear wave within the target region. The probe 712 is configured to transmit tracking pulses 703 for tracking the propagation of the shear wave within the tissue (e.g., for estimating the velocity of the shear wave and thus the tissue stiffness of at least a portion of the target region). Shear wave velocity and tissue stiffness may be estimated by the shear wave processor 742, which may be configured to implement any currently known or later developed shear wave elastography technique. The system 710 also includes an actuation controller 744, which may be separate from or integrated with the ultrasound scanner. In some embodiments, the functionality of the actuation controller 710 may be programmed into an existing processor of the ultrasound system, for example in the signal processor 726 or the shear wave processor 742. The actuation controller may perform functions as described herein, e.g., with reference to FIGS. 1 and 4-6 to control the application of the external mechanical vibrations.

Figure 8:
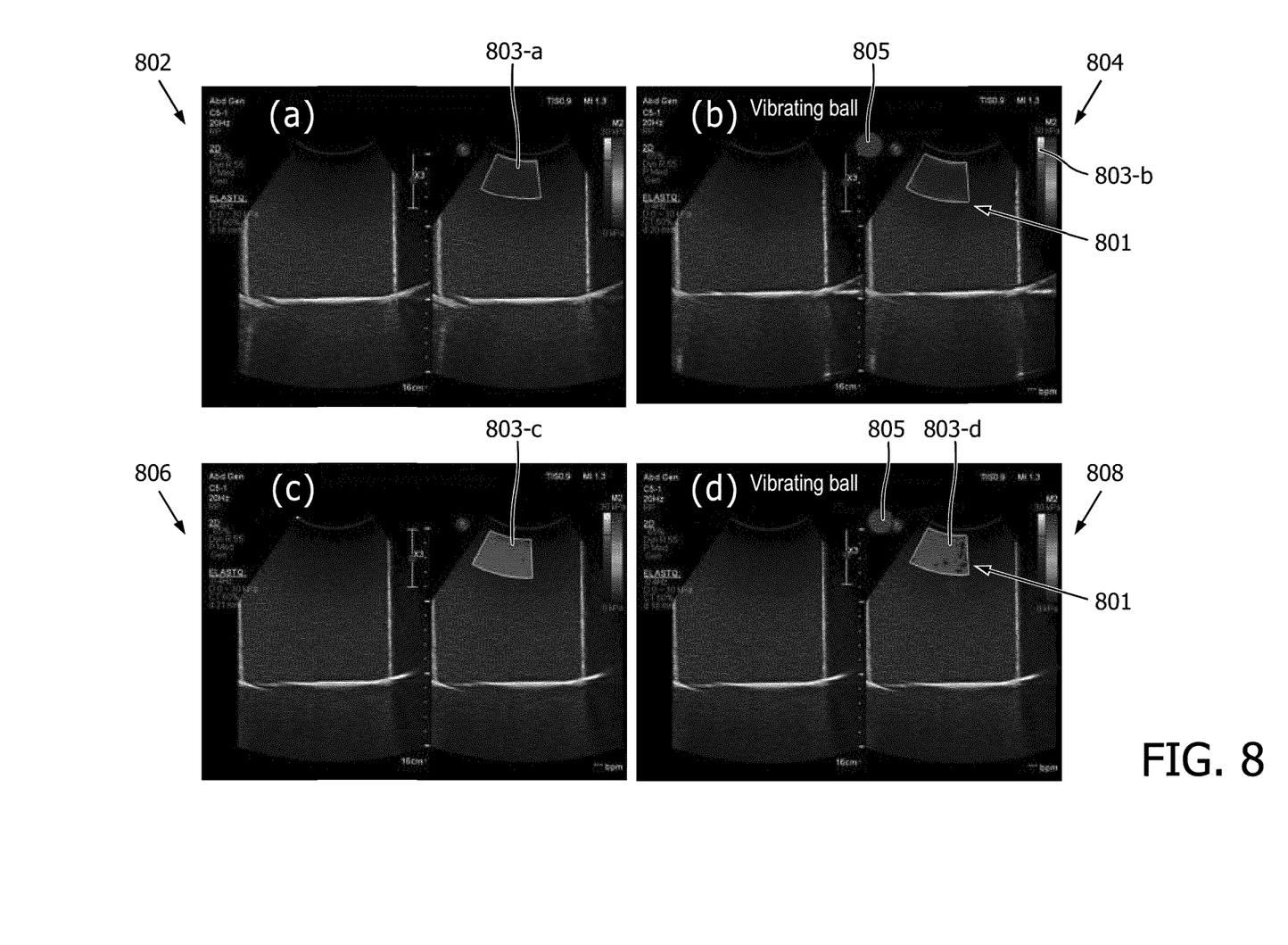
FIG. 8 shows image displays of shear wave imaging in accordance with the principles of the present disclosure.
Figure 9:
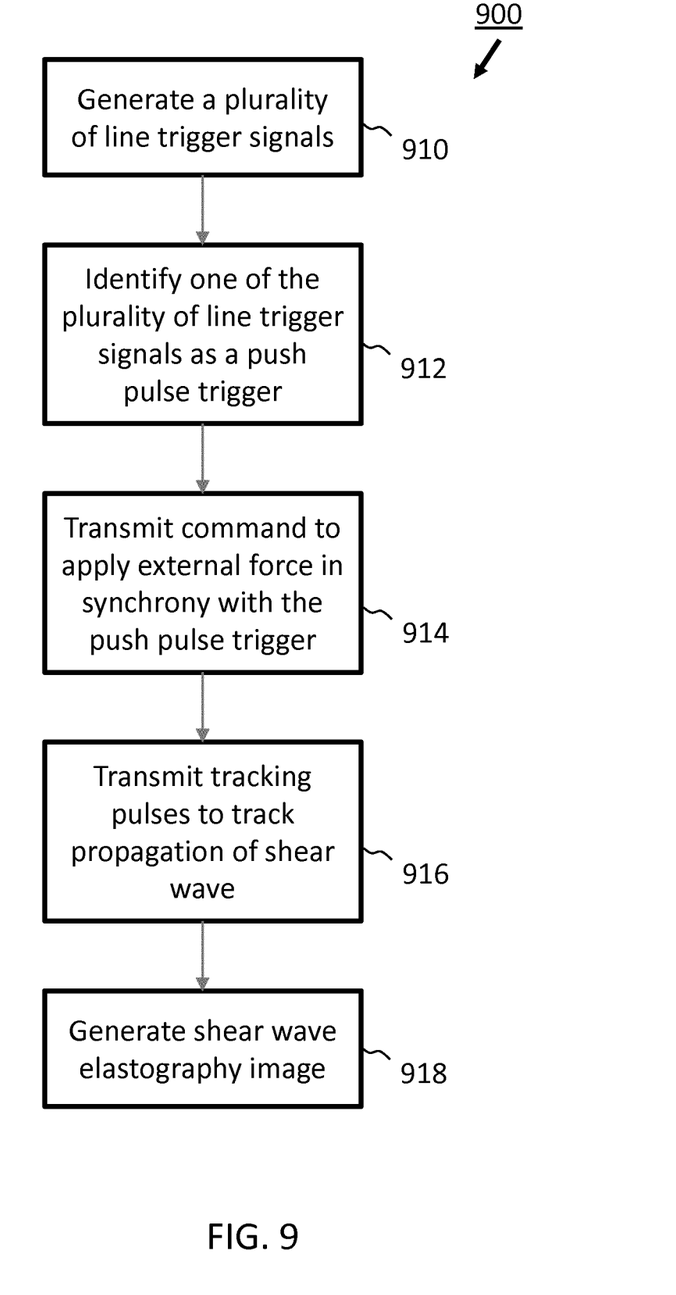
FIG. 9 shows a flow diagram of a method according to principles of the present disclosure.

FIG. 8 shows screen captures of shear wave images generated in accordance with principles of the present disclosure. The different panels (a-d) in FIG. 9 illustrate a comparison of shear wave imaging results between conventional ARF-based imaging (in panels a and c) and EMV-based SWE (in panels b and d) obtained from 4 kPa and 15 kPa phantoms, respectively. The images 804 and 808 in panels b and d, respectively show shear wave images of 4 kPa and 15 kPa phantoms. The location of an external ball-shaped vibrator in relation to the ROI 801 is indicated on the images as 805. That is, in the images 804 and 808, the ball-shaped vibrator is placed beside the probe within the imaging plane to induce a shear wave from the left side of the ROI 801. The images illustrate, among other things, the viability of integrating an EMV with an existing ultrasound system. For example, despite differences in the shear wave fronts (e.g., cylindrical in the case of ARF and spherical in the case of EMV), an existing SWE algorithm (in this case the ELASTQ imaging mode of a PHILIPS ultrasound system modified to operate with EMV) is capable of detecting the shear waves and reconstructing a stiffness map (803-b and 803-d) in good agreement with the stiffness maps in the corresponding images 803-a and 803-c) obtained from an ARF-based imaging session. Additional techniques may be employed to improve the quality of the EMV-based SWE images, e.g., to account for differences in the shear wave fronts. For example, a SWE processor according to the present disclosure, when operating in EMV mode may include one or more k-space directional filters configured to isolate wave fronts at each of the principle directions, depending on the number and arrangement of end-effectors used. Alternatively or additionally, high frame rate 2D motion tracking and shear wave reconstruction may be performed individually (e.g., for each principal wave front propagation direction) and compounded to form a final stiffness map, which may be accompanied with a shear wave confidence map e.g., as described in commonly-assigned pending application, titled "Systems, methods, and apparatuses for confidence mapping of shear wave imaging," naming Hua Xie, Jean Luc Robert, et al. as inventors.

FIG. 9 shows a flow diagram of a method according to principles of the present disclosure. The method 900 may include the steps of generating a plurality of line trigger signals (block 910), identifying one of the line trigger signals as a trigger signal associated with a push pulse (block 912), transmitting a command to an actuator to apply an external force against the subject in synchrony with the push pulse trigger signal (block 914), and transmitting tracking pulses to track the propagation of a shear wave induced by the externally applied push pulse for generating a shear wave elastography image (blocks 916 and 918). The blocks and arrangement thereof shown in FIG. 9 are merely illustrative, and other variations, including eliminating blocks, combining blocks, rearranging blocks, adding and/or substituting blocks are all contemplated.

As described herein, the line trigger signals may be generated by an ultrasound scanner which is configured to generate such line trigger signals for controlling operation of the probe (e.g., for controlling the transmission and reception of signals by the probe). One or more of the line trigger signals may be associated with a push pulse. In some embodiments in which the ultrasound scanner is also capable of producing an ARF-based pulse, the push pulse line trigger may be used to command the probe to generate such a pulse. In some embodiments, when the scanner is coupled to an external vibrator, the internal push pulses may be suppressed (e.g., by the operator of the scanner) and the external vibrator may instead be used to incite the shear waves in synchrony with the push pulse triggers. In yet further examples, the scanner may not be otherwise configured to produce an ARF push pulse but may nonetheless be programmed to generate line trigger signals in the appropriate sequence for performing shear wave imaging. Such systems may be operatively coupled to a actuation system and a controller which commands the actuation system to apply an external force to the subject to induce a shear wave, with the scanner then utilizing existing processing routines to estimate the shear wave velocity and produce the elastography image.

In some embodiments, the step of identifying the first trigger signal may include computing a time gap between a current trigger signal and a preceding trigger signal, comparing the computed time gap to a predetermined threshold value and identifying the current trigger signal and the first trigger signal upon a determination that the time gap exceeds the predetermined threshold value. Different threshold values may be preset or user configured depending on the imaging application (e.g., depending on the type of tissue being imaged, such as cardiac, liver or other). In some embodiments, the method 900 may also include a step of coupling a control signal representative of the command to a feedback logic circuit (e.g., a PID controller), which may be provided in the actuation controller, to reduce the error between from the command and a measured output of the actuator. The method 900 may also include steps for acquiring B-mode image data, e.g., according to conventional techniques, and coupling the B-mode image data with the shear wave image data to a display of the ultrasound scanner for concurrently displaying the elastography image with the anatomy image. As described throughout the present disclosure, additional or different combinations of steps may be involved in performing methods according to the principles of the present invention.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure, it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

As will be appreciated, the present methods, systems, and apparatuses may be applied to existing imaging systems such as, for example, ultrasonic imaging systems provided by PHILIPS ultrasound, which may, for example, also support a ARF-based SWE imaging, and wherein the ARF pulses may be suppressed (e.g., by preprogramming or user configuration in the field) and replaced by external mechanical excitations. Certain additional advantages and features of this invention may be apparent to those skilled in the art upon studying the disclosure, or may be experienced by persons employing the novel system and method of the present invention, chief of which is reduction of noise from off-axis signals by ultrasound imaging systems and method of operation thereof is provided. Another advantage of the present systems and method is that conventional medical imaging systems may be easily upgraded to incorporate the features and advantages of the present systems, devices, and methods. Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound shear wave elastography (SWE) system comprising:
   a probe configured to transmit ultrasound signals toward a target region of a subject and receive echo signals responsive to the ultrasound signals;
   an actuation assembly coupled to the probe and configured to apply an external force against the subject for generating a shear wave within the target region;
   an actuation controller coupled to the actuation assembly and configured to control command the actuation assembly to apply the external force responsive to a first line trigger signal; and
   an ultrasound scanner coupled to the probe and the actuation controller,
   wherein the ultrasound scanner is configured to generate a plurality of line trigger signals, comprising a plurality of second line trigger signals generated for controlling the probe to transmit a series of tracking pulses toward the target region and the first line trigger signal for generating the shear wave within the target region,
   wherein the actuation controller is configured to receive the first line trigger signal and the plurality of second line trigger signals from the ultrasound scanner,
   wherein the first line trigger signal is generated by the ultrasound scanner at a time that is a first time gap after the plurality of second line trigger signals, the first time gap being longer than a second time gap between consecutive second line trigger signals of the plurality of second line trigger signals,
   wherein the ultrasound scanner comprises at least one processor configured to generate an elastography image based at least in part on the echo signals, and
   wherein the actuation controller coupled to the actuation assembly is configured to extract the first line trigger signal from the plurality of line trigger signals generated by the ultrasound scanner and identify the first line trigger signal.

2. The system of claim 1, wherein the actuation assembly comprises at least one end effector configured to move relative to the probe to apply the external force against the subject.

3. The system of claim 2, wherein the actuation assembly further comprises:
   a frame movably joining the least one end effector to the probe; and
   an actuator coupled to the at least one end effector and configured to drive the end effector toward and away from the subject.

4. The system of claim 3, wherein the actuator comprises a voice coil actuator.

5. The system of claim 3, further comprising a linear bearing joining the end effector to a stationary portion of the frame.

6. The system of claim 2, wherein the at least one end effector comprising a pair of end effectors arranged on opposite sides of the probe.

7. The system of claim 2, wherein the controller comprises a feedback logic circuit configured to reduce an error signal based on commanded and actual displacements of the end effector.

8. The system of claim 1, wherein the actuation controller is configured to determine a third time gap between each incoming line trigger signal of the plurality of line trigger signals and a preceding line trigger signal of the plurality of line trigger signals and to identify the first line trigger signal responsive to a determination that the third time gap exceeds a predetermined threshold value.

9. The system of claim 1, wherein the actuation controller is configured to retrieve one of a plurality of predetermined threshold values responsive to a selection of an imaging application.

10. A method of shear wave imaging comprising:
    generating, by an ultrasound scanner operatively associated with a probe, a plurality of line trigger signals, comprising a first line trigger signal for generating a shear wave within a target region and a plurality of second line trigger signals generated for controlling the probe to transmit a series of tracking ultrasound pulses toward the target region, wherein the first line trigger is generated by the ultrasound scanner at a time that is a first time gap after the plurality of second line trigger signals, the first time gap being longer than a second time gap between consecutive second line trigger signals of the plurality of second line trigger signals;
    receiving the plurality of line trigger signals by an actuation controller and from the ultrasound scanner, wherein the actuation controller is communicatively coupled to an actuator coupled to the probe;
    identifying and extracting, by the actuation controller, the first line trigger signal from the plurality of line trigger signals; and
    responsive to the first line trigger signal, transmitting a command, by the actuation controller and to the actuator to apply an external force against a medium being imaged;
    transmitting the series of tracking ultrasound pulses and receiving echo signals by the probe to track propagation of the shear wave, wherein the shear wave is induced by the application of the external force; and
    generating a shear wave image data, based at least in part, on the received echo signals.

11. The method of claim 10, further comprising coupling a control signal representative of the command to a feedback logic circuit to reduce an error signal computed from the command and a measured output of the actuator.

12. The method of claim 11, wherein the feedback logic circuit implements a proportional-integral-derivative (PID) controller.

13. The method of claim 10, further comprising comparing a third time gap between a current line trigger signal of the plurality of line trigger signals and a preceding line trigger signal of the plurality of line trigger signals to a predetermined threshold value, wherein the current line trigger signal is identified as the first line trigger signal responsive to a determination that the third time gap exceeds the predetermined threshold value.

14. The method of claim 13, wherein the transmitting of at least some of the tracking ultrasound pulses occurs upon determination that the third time gap is less than or equal to the predetermined threshold value.

15. The method of claim 13, further comprising selecting one of a plurality of stored threshold values responsive to an indication of a selected imaging application and using the selected threshold value as the predetermined threshold value when identifying the first line trigger signal.

16. The method of claim 10, further comprising controlling the probe to transmit ultrasound pulses configured to acquiring B-mode image data response to at least some of the plurality of line trigger signals.

17. The method of claim 16, further comprising generating a B-mode image based on the B-mode image data and concurrently displaying the B-mode image with the shear wave image data.

* * * * *